(12) United States Patent
Sengupta et al.

(10) Patent No.: US 7,049,616 B2
(45) Date of Patent: May 23, 2006

(54) METHODS, APPARATUS, AND SOFTWARE FOR ADJUSTING THE FOCAL SPOT OF AN ELECTRON BEAM

(75) Inventors: Souma Sengupta, Belmont, CA (US); Erik William Chell, Oakland, CA (US); Sanjay Kumar Jha, Brisbane, CA (US)

(73) Assignee: General Electric Company, Schenectady, NY (US)

( * ) Notice: Subject to any disclaimer, the term of this patent is extended or adjusted under 35 U.S.C. 154(b) by 103 days.

(21) Appl. No.: 10/847,513

(22) Filed: May 17, 2004

(65) Prior Publication Data
US 2005/0253065 A1     Nov. 17, 2005

(51) Int. Cl.
*A61N 5/10* (2006.01)
(52) U.S. Cl. ............. 250/505.1; 250/310; 250/397; 250/492.1; 250/370.09
(58) Field of Classification Search ............ None
See application file for complete search history.

(56) References Cited

U.S. PATENT DOCUMENTS

| 3,895,234 | A | | 7/1975 | O'Keeffe et al. |
| 4,521,901 | A | | 6/1985 | Rand |
| 4,631,741 | A | * | 12/1986 | Rand et al. ............. 378/10 |
| 5,224,137 | A | | 6/1993 | Plomgren et al. |
| 5,633,906 | A | | 5/1997 | Hell et al. |
| 2003/0169849 | A1 | * | 9/2003 | Smyth ................. 378/113 |
| 2005/0078801 | A1 | * | 4/2005 | Georgeson et al. ....... 378/207 |
| 2005/0080596 | A1 | * | 4/2005 | Duckert et al. ......... 702/184 |

* cited by examiner

*Primary Examiner*—Nikita Wells
*Assistant Examiner*—Jaames J. Leybourne
(74) *Attorney, Agent, or Firm*—Carl B. Horton, Esq.; Armstrong Teasdale LLP

(57) ABSTRACT

A method of adjusting a beam spot width includes scanning a phantom with an electron beam having a beam spot width to obtain data; and adjusting the beam spot width using the obtained data.

28 Claims, 11 Drawing Sheets

METHODS, APPARATUS, AND SOFTWARE FOR ADJUSTING THE FOCAL SPOT OF AN ELECTRON BEAM

BACKGROUND OF THE INVENTION

This invention relates generally to the field of electron beam computed tomography. More particularly, the present invention relates to methods for increasing the resolution of electron beam computed tomography scanners.

Electron beam computed tomography (EBCT) is a non-invasive imaging technique for capturing images of human organs. To capture images by using an EBCT scanner, a focused electron beam is directed onto tungsten targets. The focusing is done with the help of a focusing system. Due to the impinging of the electron beam, X-rays are produced at the tungsten targets. These X-rays are directed at semi-circular detectors. The X-rays pass through the object, which is to be imaged, and are collected by the detectors.

The resolution of an image obtained from an EBCT scanner depends on the width of the detectors, the collimation of the electron beam, and the width of the electron beam focus spot on the targets. A non-optimal beam spot width results in lack of sharpness or blurring at the edges of the images.

One method of measuring the width of the focal spot in an EBCT scanner is by passing the electron beam over a set of 'w-wires'. This method is described in U.S. Pat. No. 5,224,137, titled "Tuning the Scanning Electron Beam Computed Tomography Scanner", filed on May 23, 1991, and assigned to Imatron Inc. The w-wires are placed on a non-imaging target. A current that depends on the width of the focal spot is generated in the w-wires as the electron beam passes over them. This current is measured and used to quantify the width of the focal spot. The current supplied to the focusing coil is adjusted to obtain an optimal beam spot width for the non-imaging target. The current is then modified to derive the optimal beam spot width for the imaging targets by using theoretical calculations.

Other methods of finding the optimal current for the focusing coil use specialized phantoms for calculating the beam spot width. Further, these methods use non-imaging targets to find the beam spot width. This means that the beam spot may have unequal widths at different points on the surface of the imaging targets, reducing the resolution of the images captured. Finally, these methods are complicated and require a substantial amount of time to calculate the beam spot width.

BRIEF DESCRIPTION OF THE INVENTION

In one aspect, a method of adjusting a beam spot width is provided. The method includes scanning a phantom with an electron beam having a beam spot width to obtain data; and adjusting the beam spot width using the obtained data.

In another aspect, an electron beam computed tomography (EBCT) system is provided. The system includes an electron beam source configured to emit an electron beam, a target positioned to be impinged with the electron beam and radiate x-rays, a detector positioned to receive the x-rays, and a computer operationally coupled to the detector and the source. The computer is configured to receive x-ray data regarding a scanned phantom, and adjust a beam spot width of the emitted electron beam using the received x-ray data.

In yet another aspect, a computer readable medium encoded with a program is provided. The program is configured to instruct a computer to repeatedly receive and analyze data regarding a scanned phantom, and repeatedly adjust a beam spot width until a substantially minimum beam spot width is obtained.

In still another aspect, a method of providing a malfunction indication is provided. The method includes repeatedly receiving and analyzing data regarding a scanned phantom, repeatedly adjusting a beam spot width attempting to obtain a desired beam spot width, and providing an indication when the desired beam spot width is unobtainable.

In yet another aspect, a method for increasing a diagnostic ability is provided. The method includes scanning an object using a first electron beam spot width to obtain first x-ray data, using the first x-ray data to obtain a second electron beam spot width less than the first electron beam spot width, and scanning a patient using the second electron beam width to obtain diagnostic data superior to that obtainable with the first electron beam spot width.

DETAILED DESCRIPTION OF THE INVENTION

The present disclosure relates to a method for adjusting the focal spot of an electron beam, using a low-precision "multipin" phantom. The electron beam can be used in a scanning electron beam computed tomography (EBCT) scanner.

Figure 1:
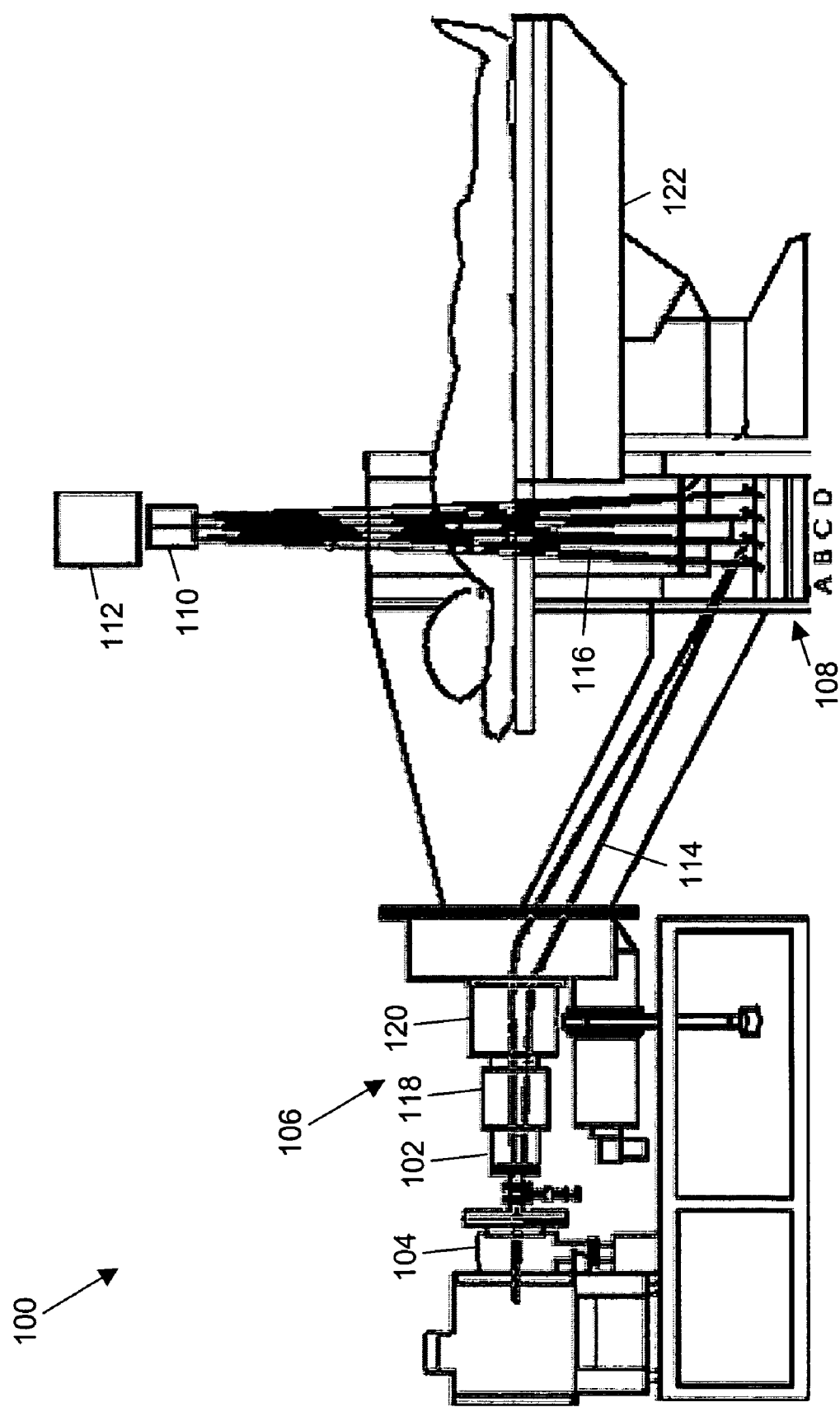
FIG. 1 is a sectional side view of a scanning electron beam computed tomography scanner.

FIG. 1 is a sectional side view of a scanning EBCT scanner 100, in which the method of the present invention can be practiced. This scanner may be identical to the scanner disclosed in U.S. Pat. No. 4,631,741, titled "Beam spot monitoring arrangement for use in a scanning electron beam computed tomography scanner and method", filed on Apr. 5, 1984, and assigned to Imatron, Inc. However, it will be apparent to those skilled in the art that the current invention can be practiced with any other EBCT scanner. Only the specific features of the scanner described in U.S. Pat. No. 4,631,741, that are directly related to the present invention, will be described in this disclosure. It should be noted that scanner 100 may include other components which do not form a part of the present invention but are necessary for the working of scanner 100.

Scanner 100 includes a vacuum chamber 102, an electron gun 104, a focusing and scanning system 106, an assembly of targets 108, an assembly of detectors 110, and a data processing system 112. Scanner 100 may further include a patient table 122, on which an object to be scanned may be placed. Electron gun 104 produces a beam of electrons 114. Electron beam 114 passes through vacuum chamber 102 and is focused by scanning and focusing system 106 so that it impinges on a target in assembly of targets 108. An X-ray 116 is produced due to the impinging of electron beam 114 on assembly of targets 108. The targets in assembly of targets 108 are positioned in such a way that X-ray 116 is directed at assembly of detectors 110. X-ray 116 passes through the object, which has to be imaged, and reaches a detector in assembly of detectors 110. The detector measures the distribution of intensity of X-ray 116. This intensity distribution is digitized and processed by data processing system 112.

Scanning and focusing system 106 further includes a solenoid coil 118 and an assembly of focus coils 120, that are responsible for focusing electron beam 114 and sweeping electron beam 114 across assembly of targets 108. Though the system for scanning and focusing referred to in this disclosure is of the type described above, it will be apparent to those skilled in the art that any other system could be used to affect the scanning and focusing of electron beam 114. For example, an electrical field focusing device could be used to scan and focus electron beam 114.

Figure 2:
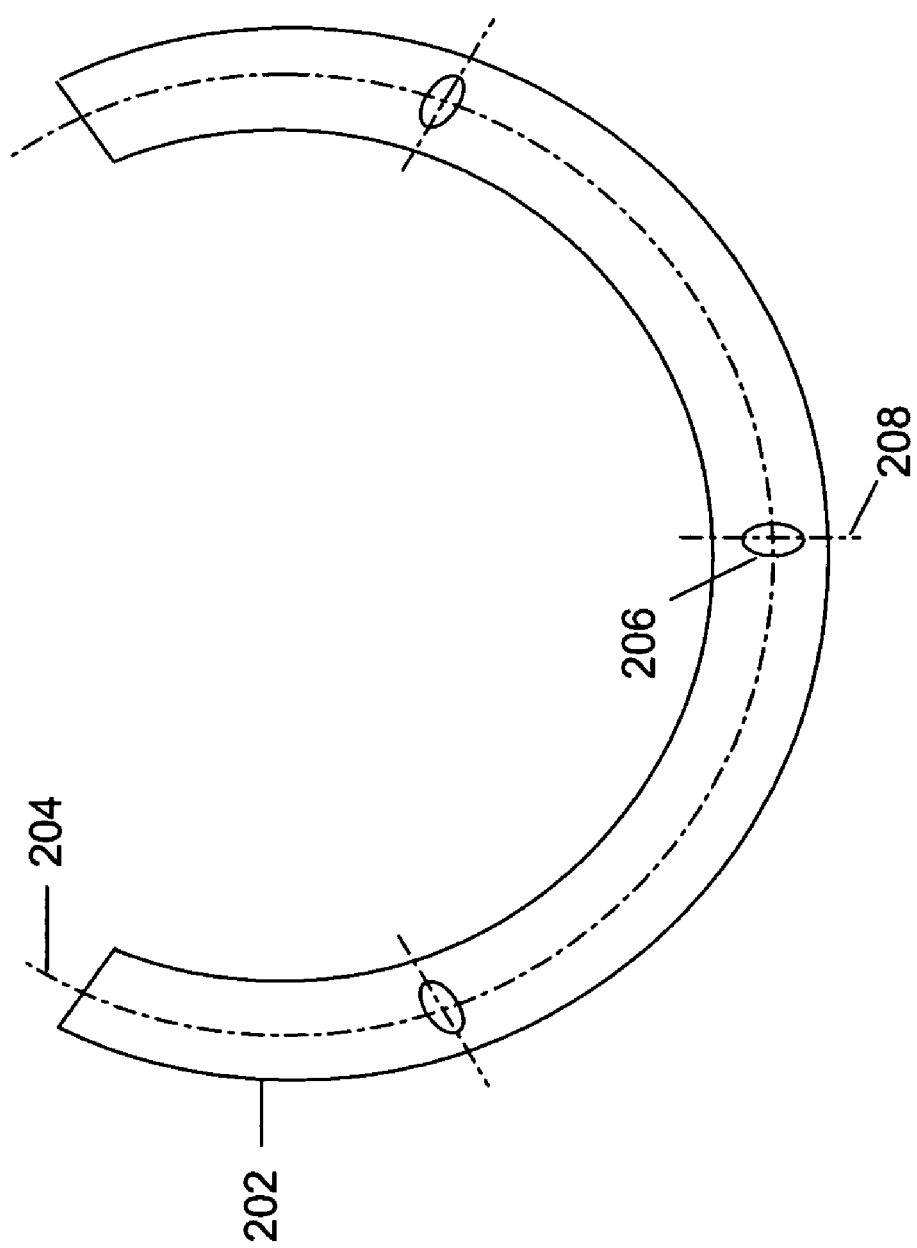
FIG. 2 is a sectional front view of a target of the electron beam computed tomography scanner.

FIG. 2 is a front view of a target 202 of assembly of targets 108 (as shown in FIG. 1). Electron beam 114 (as shown in FIG. 1) moves along azimuthal axis 204 of detector 202. A cross-section 206 of electron beam 114, as it moves across target 202, is shown as elliptical. The major axis of the elliptical section is along radial direction 208. The minor axis of the elliptical section is along azimuthal axis 204. Cross section 206 is created by assembly of focus coils 120 (as shown in FIG. 1) that focuses electron beam 114 to a spot on target 202 utilizing differential focal strength optics.

Figure 3B:
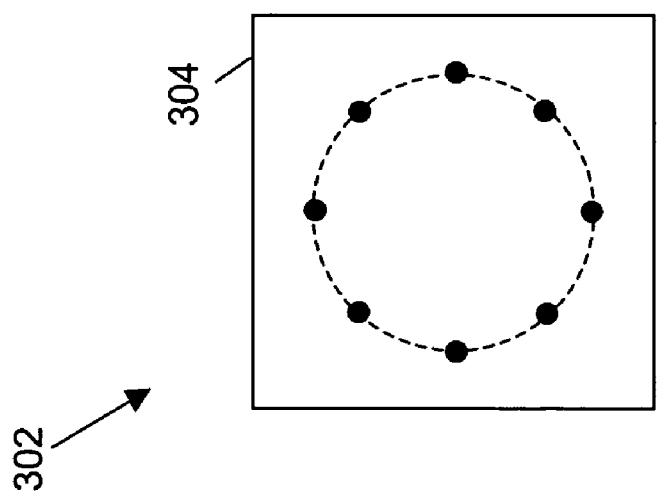
FIG. 3A and FIG. 3B are side and front views of a multipin phantom.
Figure 3A:
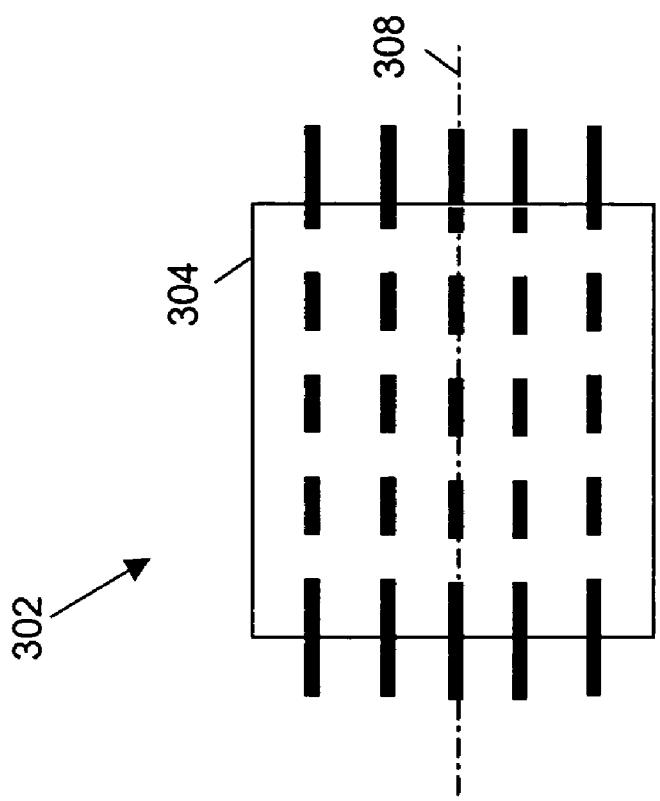

In accordance with an embodiment of the present invention, a multipin phantom is used to adjust the spot of electron beam 114. FIG. 3A and FIG. 3B are block diagrams illustrating an exemplary multipin phantom 302. FIG. 3A shows the side view and FIG. 3B the front view of multipin phantom 302. Multipin phantom 302 includes a cuboidal block of foam 304 and at least one rod or pin passing through foam block 304. For example, FIG. 3A shows eight rods 306 passing through foam block 304. Rods 306 are arranged approximately in a circle and are aligned along axis 308, which is the direction in which electron beam 114 (as shown in FIG. 1) travels. In accordance with one embodiment of the invention, another rod is placed in the center of the circle defined by rods 306. An exemplary material, which rods 306 are made of, is tungsten. It will be apparent to those skilled in the art that rods 306 can also be made of steel or any other material that has high density to X-rays.

Multipin phantom 302 is placed on patient table 122 (as shown in FIG. 1) so that axis 308 is along the axis of scanner 100 (as shown in FIG. 1), i.e., with rods 306 pointing towards electron gun 104 (as shown in FIG. 1). No accuracy is required in placing multipin phantom 302. The width of the spot of electron beam 114 is calculated by data processing system 112 (as shown in FIG. 1), based on data obtained during the scanning of multipin phantom 302. Based on the measured value of the width of the electron beam spot, the current supplied to assembly of focus coils 120 is adjusted to obtain an optimal value of electron beam spot width.

Figure 4A:
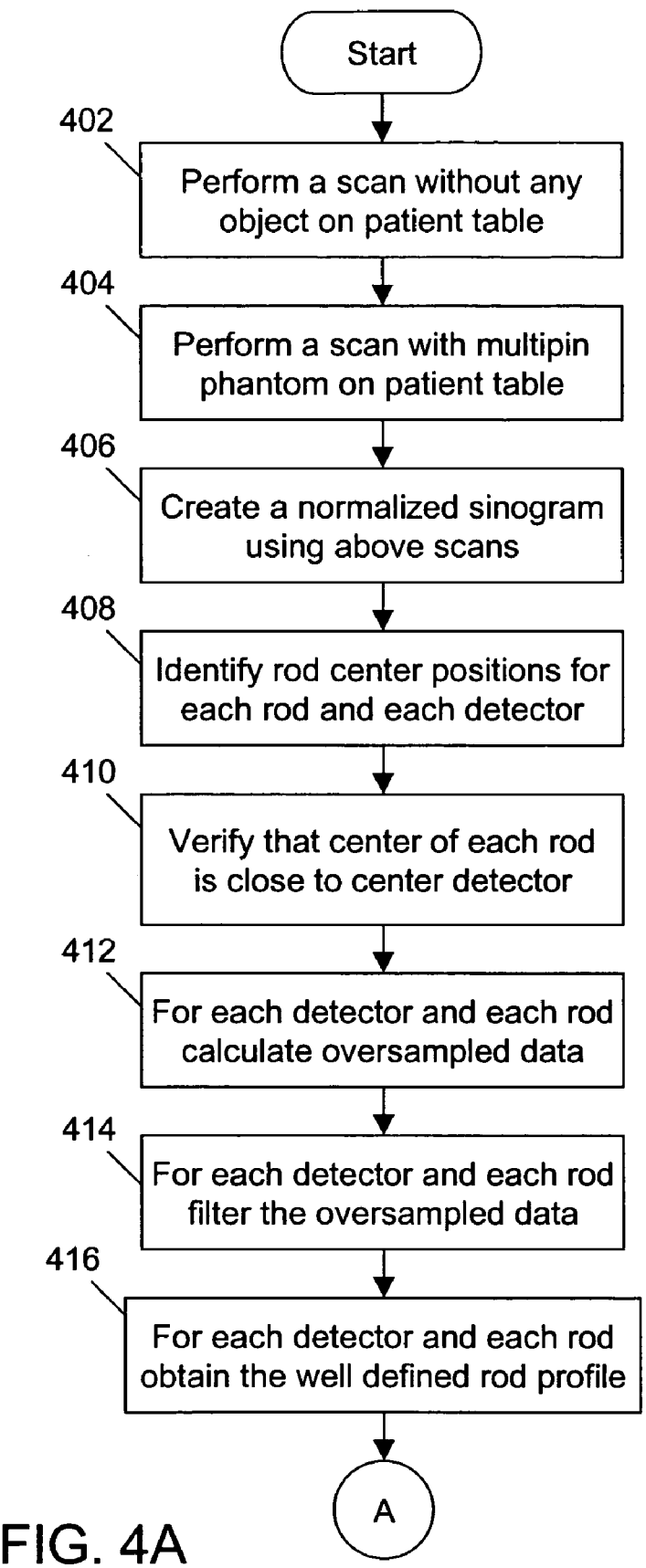
FIG. 4A and FIG. 4B illustrate a flowchart showing the steps for obtaining an optimal value of an electron beam spot.
Figure 4B:
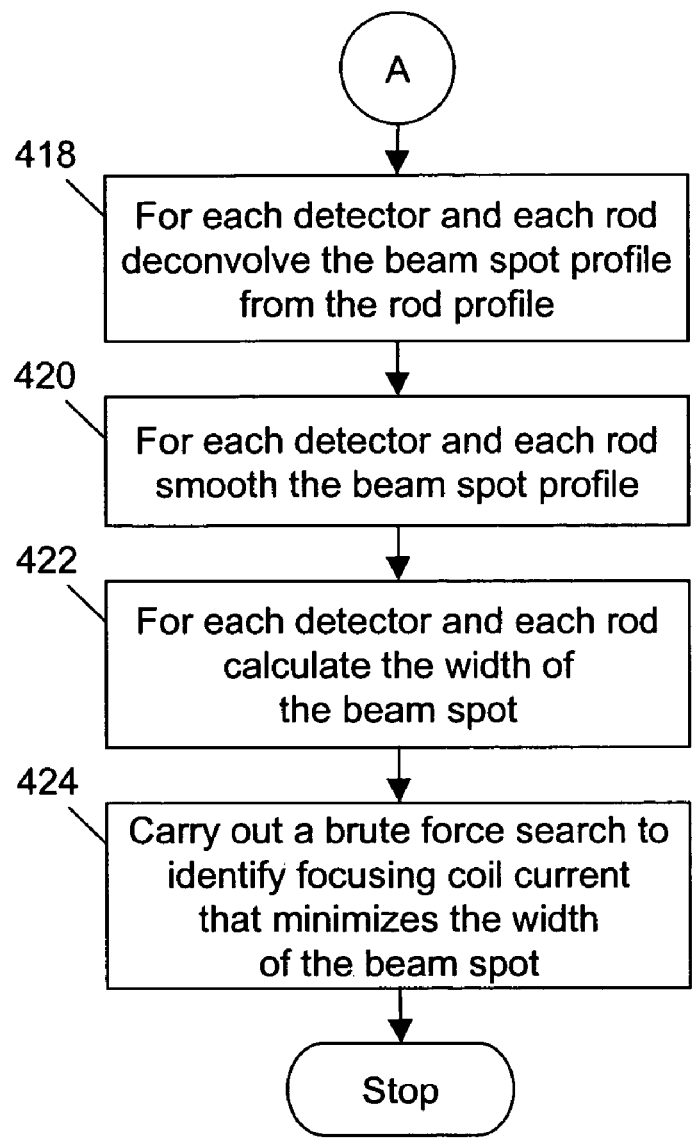

FIG. 4A and FIG. 4B illustrate a flowchart showing the steps for obtaining an optimal value of the electron beam spot. At step 402, a scan is performed, without any object on patient table 122 (as shown in FIG. 1). At step 404, another scan is performed with multipin phantom 302 (as shown in FIG. 3A) on patient table 122. Data processing system 112 (as shown in FIG. 1) digitizes the intensity distribution obtained during the scans. Using the digitized data obtained during the scans performed at steps 402 and 404, a normalized sinogram is created at step 406. The positions of the centers of rods 306 are identified, using data obtained at each of the detectors of detector assembly 110 (as shown in FIG. 1), at step 408. At step 410, it is verified that the position of the rod centers is close to the center samples of the detectors. Steps 412, 414, 416, 418, 420, and 422 are carried out, using data obtained for each rod of rods 306 in multipin phantom 302 at each detector in assembly of detectors 110. At step 412, data for rods 306 (as shown in FIG. 3A) is oversampled using samples from multiple detectors. These oversampled data are filtered, to reduce noise at step 414. Profiles of rods 306 are obtained from the oversampled and smoothed data at step 416, and the beam spot profiles are deconvolved from the profiles of the rod at step 418. The deconvolved beam spot profiles are smoothened at step 420. The width of the beam spot is calculated at step 422. Finally, at step 424, a search to find a set of coil currents that minimizes the width of the beam spot width is carried out.

Figure 5:
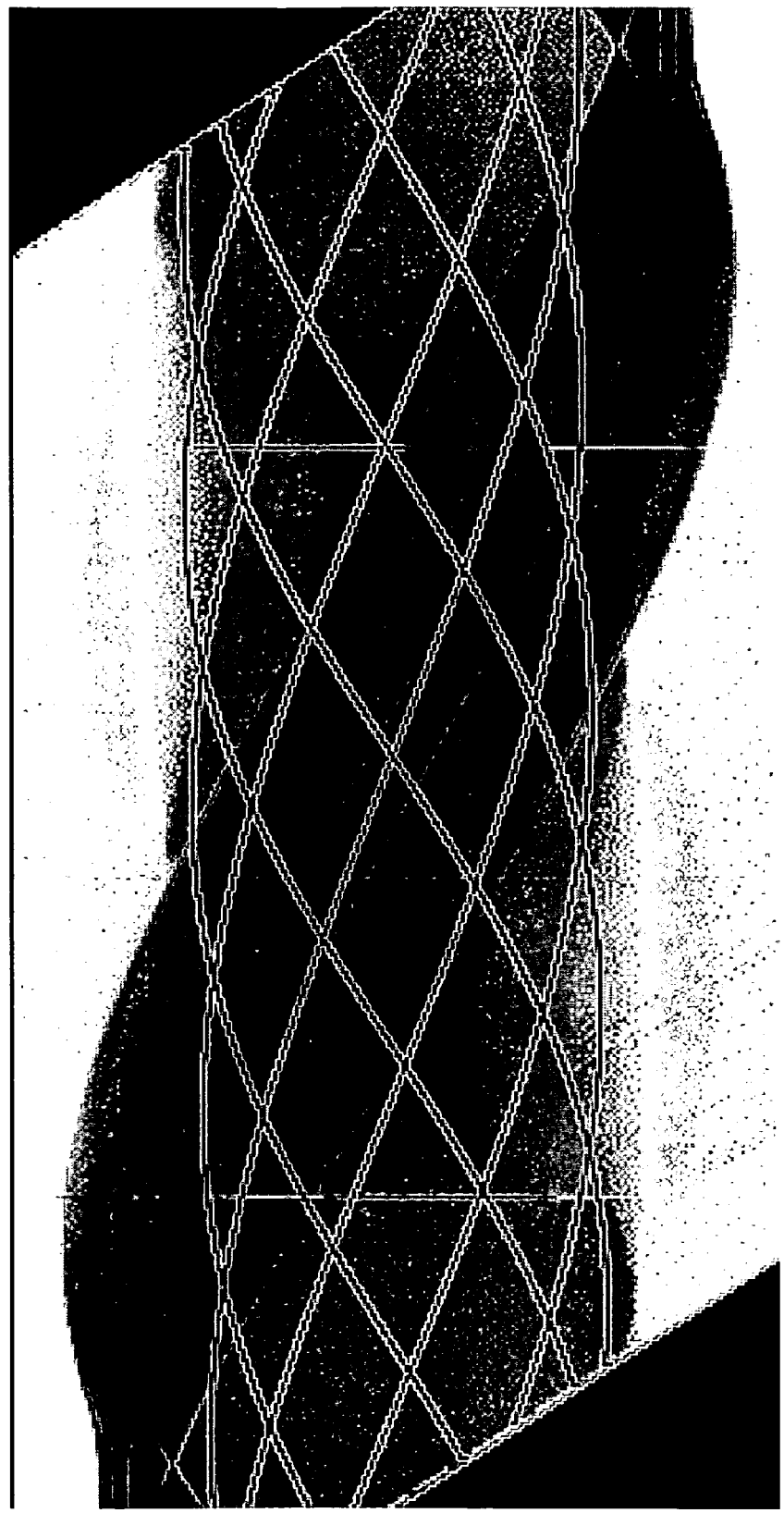
FIG. 5 is an illustration of a normalized sinogram for a multipin phantom with eight rods.
Figure 6:
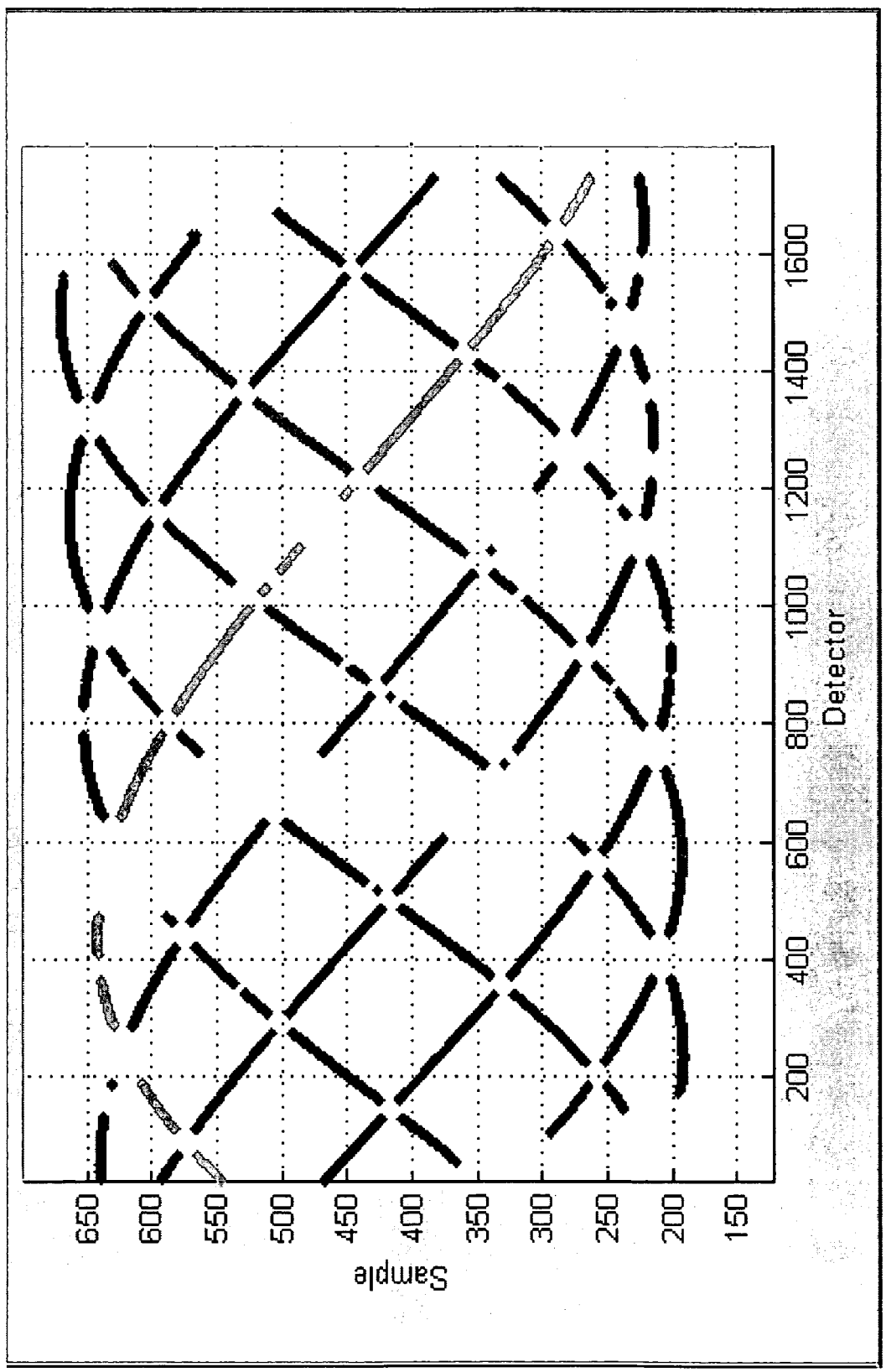
FIG. 6 is a graph illustrating the positions of the centers of rods.

The sinograms obtained at steps 402 and 404 are two-dimensional matrices comprising intensity values of X-rays, which are sampled by detectors in assembly of detectors 110. The sinogram is a matrix of samples collected by each detector. The sinograms obtained at steps 402 and 404 are hereinafter referred to as $[A_{d,s}]$ and $[B_{d,s}]$, respectively, where 'd' is an index for the detectors and is an index for the samples. The normalized sinogram is created at step 406 by taking a ratio of the corresponding elements of $[B_{d,s}]$ and $[A_{d,s}]$, and is referred to as $[S_{d,s}]$. Therefore, $[S_{d,s}]$ is also a two-dimensional array. FIG. 5 is an illustration of a normalized sinogram for a multipin phantom with eight rods. Each of the curved lines in FIG. 5 represents a rod. The centers of the shadows of rods 306 are located at step 408. The exact sample numbers of the centers of the shadows of rods 306 are obtained by convolving a ramp to the signal of the normalized sinogram, and looking at the zero crossing of the convolved signal. Shadows of rods 306 appear as impulses in the normalized sinogram. On convolving the normalized sinogram with the ramp, the convolved signal goes through the zero crossing at the center of the pin. This technique can be used to identify the sample numbers for the centers of rods 306. The rod positions for all the detectors are stored as a two-dimensional matrix $[P_{i,j}]$, where 'i' is an index for the detectors and 'j' is an index for rods 306. FIG. 6 is a graph illustrating the positions of centers of rods 306. The graph is a plot of the sample number at which the pin center is located against the detector at which the sample is taken. Each of the lines represents the variation of the location of one rod center across the various detectors of detector assembly 110. The discontinuities in the graph are points of overlap of centers of rods 306. Data corresponding to these centers is considered invalid as it cannot be used to estimate the width of the beam spot. Hence, it is marked with a flag to indicate that it is invalid. Data marked with a negative flag will not be considered for estimating the beam spot width. At step 410 (as shown in FIG. 4), it is verified that the centers of rods 306, i.e., [Pi,j], are close to the center samples of the detectors. This ensures that multipin phantom is in the center of scanner 100.

At step 412 (as shown in FIG. 4), oversampled data are calculated for each detector of assembly of detectors 110 and each rod of multipin phantom 302. To estimate the beam spot width, well defined profiles of rods 306 are required. This requires a significant number of samples in the shadows of rods 306 as the beam spot disappears behind rods 306. However, the speed of electron beam 114 is too high and the beam spot is too narrow to get enough samples. Therefore, the data obtained at each detector in the normalized sinogram is not enough to estimate the width of the beam spot. Hence, the data is oversampled using samples from multiple detectors. The steps involved in obtaining the oversampled data are described later in conjunction with FIG. 10.

Figure 7:
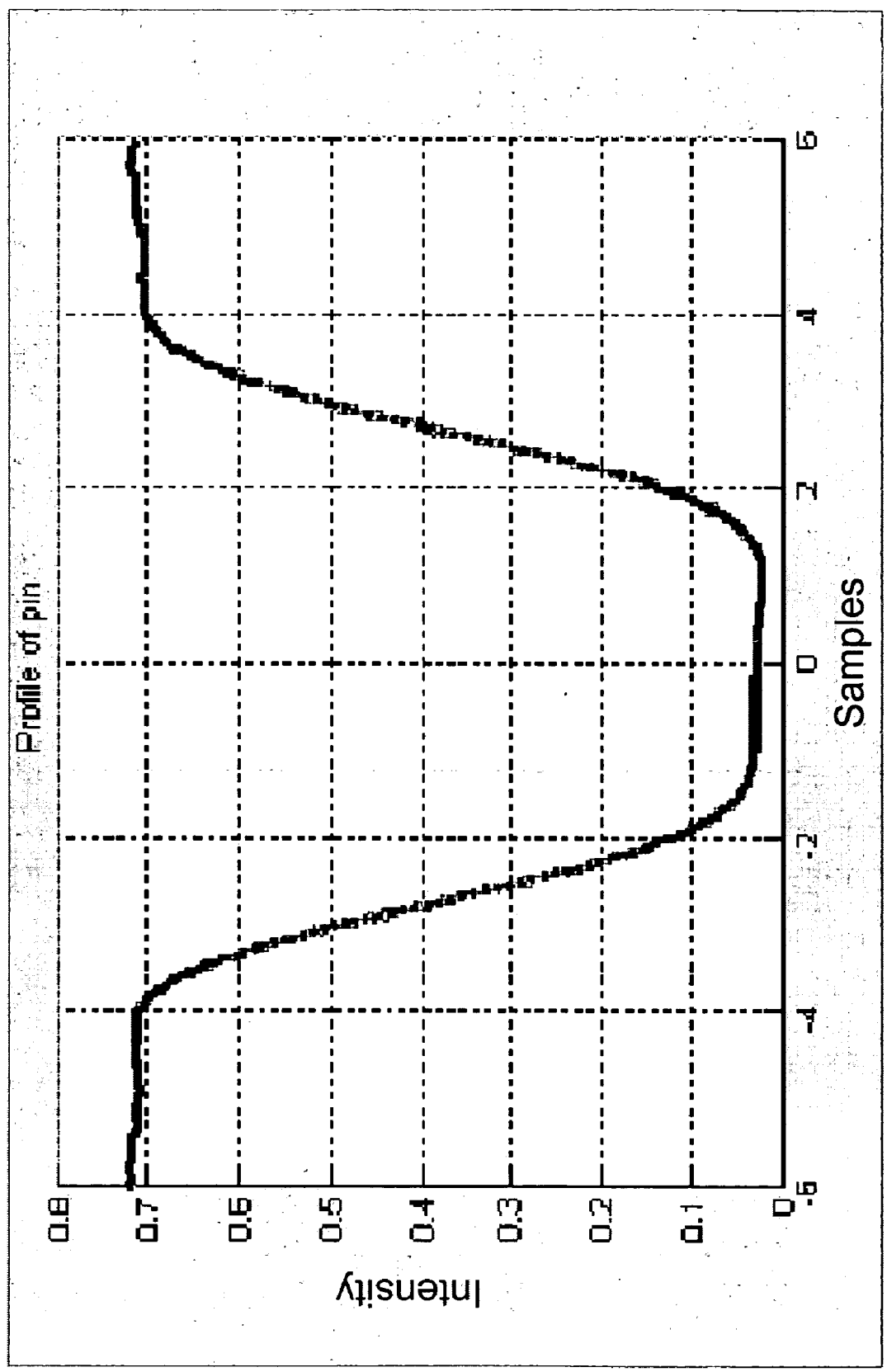
FIG. 7 is a graph illustrating the profile of a rod after resampling.
Figure 8:
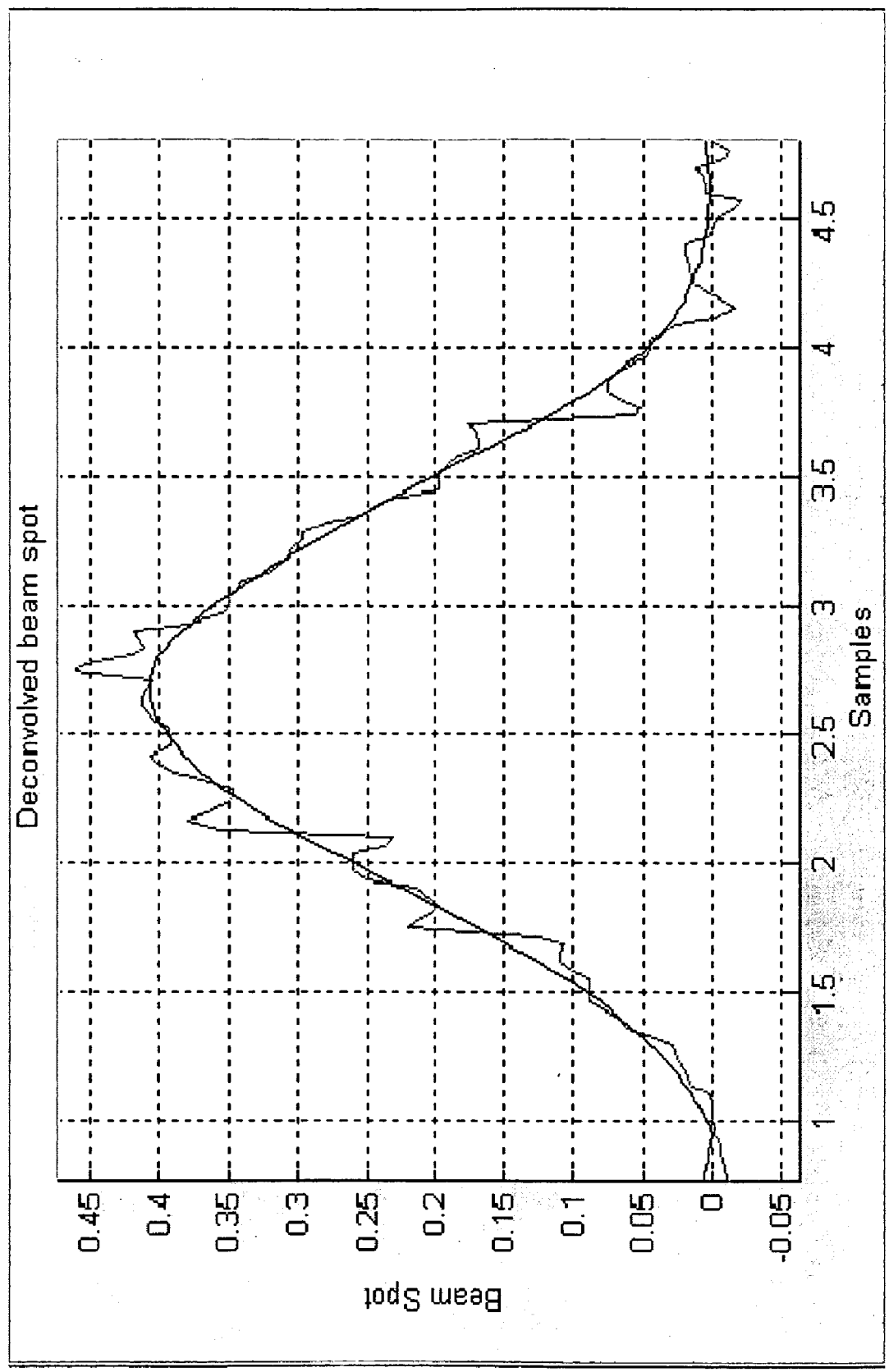
FIG. 8 is a graph illustrating a deconvolved beam spot profile and a smoothed beam spot profile.

At step 414, the oversampled data is filtered to remove unwanted high frequency noise. In accordance with one embodiment of the present invention, 3-point smoother filtering of the data is done in order to remove unwanted high frequency noise. This is done at step 414. At step 416, a well-defined profile of each rod of rods 306 is obtained. This is accomplished by resampling the oversampled and smoothed data at equal intervals of time. FIG. 7 is a graph illustrating the profile of a rod after resampling the data. The graph shows the variation of the intensity obtained at one detector against the samples. Since rods 306 are thick, each rod profile has 2 edges, one when the beam spot goes behind a rod and another when the beam spot comes out from behind the rod. Further, at step 418, beam spot profiles are obtained from the rod profiles. This is done by deconvolving the beam spot profile from the rod profiles. Each edge in every rod profile is used to get a beam spot profile. The beam spot profiles are smoothed at step 420. FIG. 8 is a graph illustrating the deconvolved beam spot profile (shown in lighter shade) obtained at step 418 and the smoothed beam spot profile (shown in darker shade) obtained at step 420. In accordance with one embodiment of the present invention, the beam spot profiles are smoothed such as by using a square filter or a 3-point smoother.

Figure 9:
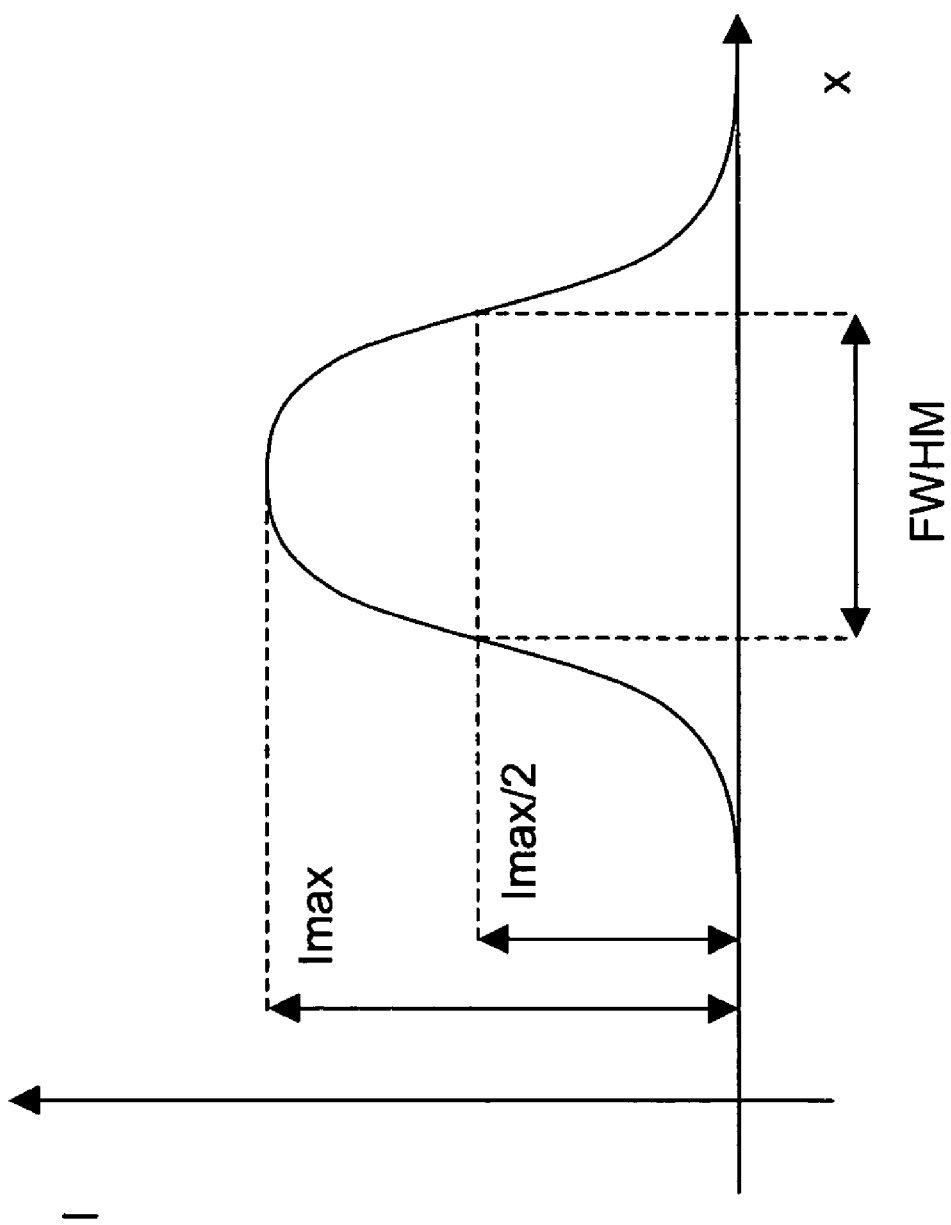
FIG. 9 is a graph of a beam spot profile illustrating the calculation of the width of the beam spot, using full width half maximum of the beam spot profile.

The width of the beam spot is calculated at step 422. In an embodiment of the invention, the width of the beam spot is taken to be the full width half maximum of the beam spot profiles. FIG. 9 is a graph of the beam spot profile, showing the calculation of the width of the beam spot, using full width half maximum of the beam spot profile. The horizontal axis represents a direction across the beam spot, and the vertical axis represents the intensity of the beam spot. The maximum intensity of the beam spot is represented by $I_{max}$. The width in the horizontal axis corresponding to the intensity value of $I_{max}/2$ is the full width half maximum represented by FWHM. It will be apparent to those skilled in the art that the width of the beam spot may be obtained through other measurements also. For example, the beam spot width can be calculated by determining the edges of the profiles of the rods 306 from the oversampled and filtered data obtained at step 414. In another embodiment of the present invention, the width of the beam spot is calculated, using the duration of time in which the beam spot is completely occluded by a rod, i.e., the time in which the beam spot disappears behind a rod.

The beam spot width is obtained for every time in the matrix $[T'_{d,p}]$. Hence, the width can be represented as B(t) where, $t=[T'_{d,p}]$. 't' varies with the angular location of the beam spot θ in azimuthal direction according to the relation, θ=ωt B(t) also represents the variation of the width of the beam spot according to the angular location of the beam spot on assembly of targets 108. An optimal value of B(t) can be obtained by varying the current $F_c(t)$, supplied to assembly of focus coils 120 that focuses electron beam 114 on assembly of targets 108. Current $F_c(t)$ also varies with time t. A search is carried out at step 424 to find the $F_c(t)$ that minimizes B(t). In accordance with an embodiment of the present invention, a golden ratio search is carried out to vary Fc and minimize B(t). The golden ratio (φ), $$\phi = \frac{\sqrt{5}+1}{2}$$

is used to generate an estimate for $F_c(t)$ that reduces the width of the beam spot in the process of the minimization of B(t). This value of $F_c$ is supplied to assembly of focus coils 120 (as shown in FIG. 1), and the method described with the help of FIG. 4 is carried out again, i.e., the width of the beam spot is recalculated. This process is repeated iteratively till a value of $F_c(t)$ is found that minimizes the width of the beam spot.

Figure 10:
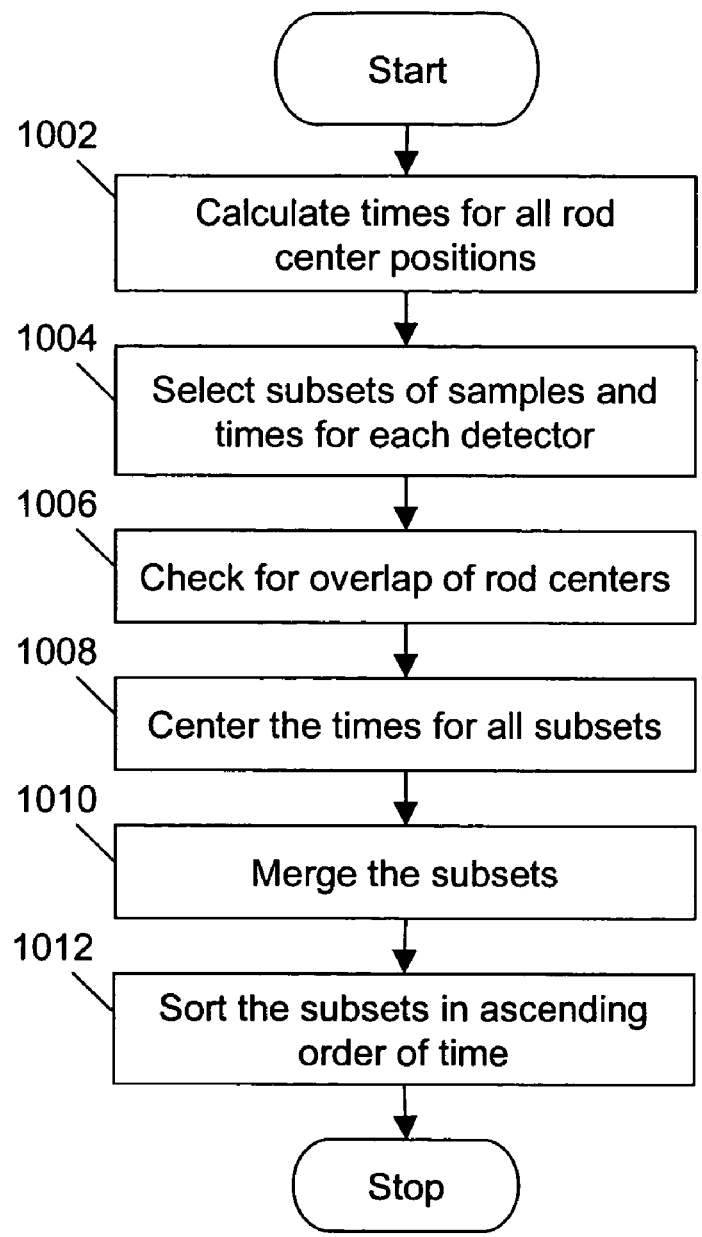
FIG. 10 is a flowchart illustrating the steps involved in calculating oversampled data.

FIG. 10 is a flowchart illustrating the steps involved in calculating the oversampled data at step 412 in FIG. 4A. At step 1002, times for all center positions of rods 306 (as shown in FIG. 3A) are calculated for each detector and some detectors on either side of each detector, i.e. for each detector d and detectors in the range $$d - \frac{n_0}{2} \ldots d + \frac{n_0}{2}$$

These are the time periods from the beginning of the revolution of electron beam 114 (as shown in FIG. 1) on target 202 (as shown in FIG. 2) to the position on target 202, where the centers of rods 306 are found. These times are obtained by dividing the angles at which rod centers are located by the speed of rotation of electron beam 114. Therefore, $$t = \frac{\theta}{\omega}$$

where θ is the position of the rod centers and ω is the speed of rotation of electron beam 114. The times are stored in a two-dimensional matrix referred to as $[T_{d,r}]$ where 'd' is an index for the detectors and 'r' is an index for rods 306. At step 1004, subsets $[S'_{d,p}]$ of samples $[S_{d,s}]$, and $[T'_{d,p}]$ of times $[T_{d,r}]$ are obtained for each detector. These subsets include samples and time values of adjacent detectors. Therefore, for each detector and each rod, $$[S'_{d,p}] = [S_{i,j}] \quad [T'_{d,p}] = [T_{i,j}]$$
$$\text{where } i = d - \frac{n_0}{2}, \ldots, d + \frac{n_0}{2} \&$$
$$j = rnd([P_{i,j}]) - \frac{n_p}{2}, \ldots, rnd([P_{i,j}]) + \frac{n_p}{2}$$

where $n_o$ and $n_p$ are appropriate numbers chosen to get oversampled data. For example, to consider 50 detectors on either side of a detector, $n_o$ can be set to 100. Similarly, to take ten samples before and after any sample, $n_p$ can be set to 20. Here, rnd( ) is the rounding off function.

At step 1006, the oversampled data is analyzed to eliminate unwanted data. More specifically, the shadows of two or more rods might overlap in some samples. Data corresponding to these shadows is considered invalid, as it does not portray the profiles of rods 306. Hence, data from all detectors is checked to ensure that rod centers do not overlap. For this, the flags set at step 408 (as shown in FIG. 4) are checked. If a flag for a rod center is set to negative, then the rod center is ignored.

The data obtained at each detector is distributed in terms of time. For example, in a series of $n_o$ detectors, the first detector samples rod shadows at time $t_1$. The next detector samples rod shadows at $t_2 = t_1 + \Delta t$, and so on. Therefore, to center the samples, all data is centered to a common time at step 1008. This is done by performing the following operation:

$$[T'_{i,p}] = [T'_{i,p}] - [T'_{d,p}] \text{ where } i = d - \frac{n_o}{2}, \ldots, d + \frac{n_o}{2}$$

Here, $[T'_{d,p}]$ is the time subset corresponding to the center detector in a series of $n_o$ detectors. Hence, all samples for the center detector are centered at time $[T'_{d,p}]$. The oversampled data includes $[S'_{d,p}]$ and $[T'_{d,p}]$. This data is then merged at step 1010. Merging can be accomplished by concatenating the matrices of the data values. Finally, the subsets are sorted in ascending order of time at step 1012. As described above, this oversampled data is used to calculate the width of the beam spot.

The methods as described above can be used to provide a malfunction indication in accordance with one embodiment of the present invention. The steps described in conjunction with FIG. 4 are carried out to obtain a desired beam spot width. However, if a desired beam spot width is not obtained after repeatedly adjusting the beam spot width, a malfunction indication is provided. For example, in case a desired beam spot width is not obtained for scanner 100, then a malfunction indication is provided. The malfunction indication can be in the form of an appropriately placed warning light on scanner 100. This light can be used to alert an operator of scanner 100 that the desired beam spot width is not obtained. The malfunction indication can also be in the form of an alert on a monitor or screen connected to data processing system 112. Further, a similar alert can be provided to the screen of another computer through a network. For example, data processing system 112 can convey an alert to the computer belonging to a technician. On receiving the alert, the technician can perform repair work on scanner 100 to ensure that the desired beam spot width is obtained.

In accordance with another embodiment of the present invention, the methods described above are used to increase the diagnostic ability of a scanner such as scanner 100. An object is scanned with the help of an electron beam having a first electron spot width to obtain X-ray data. This X-ray data is used to obtain a second beam spot width that is lesser than the original beam spot width, and hence desired. Further, an electron beam with this second electron beam spot width is used while scanning a patient. As the electron beam spot width is of a desired value, the diagnostic data obtained while scanning the patient will be superior to the diagnostic data obtained with the first beam spot width. Diagnostic data includes images generated with the help of a computed tomography scanner, such as scanner 100. Hence, the images obtained while scanning the patient with the help of an electron beam with the second beam spot width will have a higher resolution. The object used should contain an edge that is substantially centered in the field of view of the scanner. The edge is required to estimate the beam spot width. Therefore, the object can be a multipin phantom as described in conjunction with FIG. 3A. However, it will be apparent to those skilled in the art that instead of a multipin phantom, the object used to obtain the X-ray data could be a bone, a blood vessel etc., within a patient. This X-ray data can then be used to obtain the lesser beam spot width.

Data processing system 112 (as shown in FIG. 1), as described in the various embodiments of the present invention, may be embodied in the form of a computer system. As used herein, the term computer is not limited to just those integrated circuits referred to in the art as computers, but broadly refers to computers, processors, microcontrollers, microcomputers, programmable logic controllers, application specific integrated circuits, and other programmable circuits.

The computer system includes a computer, an input device, a display unit and the Internet. The computer further includes a microprocessor. The microprocessor is connected to a communication bus. The computer also includes a memory. The memory may include Random Access Memory (RAM) and Read Only Memory (ROM). The computer system further includes a storage device. The storage device can be a hard disk drive or a removable storage drive such as a floppy disk drive, CD-ROM drive, DVD drive, magnetic optical disc (MOD) device etc. The storage device can also be other similar means for loading computer programs or other instructions into the computer system. The computer system also includes a communication unit. The communication unit allows the computer to connect to other databases and the Internet through an I/O interface. The communication unit allows the transfer as well as the reception of data from other databases. The communication unit may include a modem, an Ethernet card, or any similar device, which enables the computer system to connect to databases and networks such as LAN, MAN, WAN and the Internet. The computer system facilitates inputs from a user through an input device, accessible to the system through I/O interface.

The computer system executes a set of instructions that are stored in one or more storage elements, in order to process input data. The storage elements may also hold data or other information, as desired. The storage element may be in the form of an information source or a physical memory element present in the processing machine.

The set of instructions may include various commands that instruct the processing machine to perform specific tasks such as the steps that constitute the method of the present invention. The set of instructions may be in the form of a software program. Further, the software may be in the form of a collection of separate programs, a program module with a larger program, or a portion of a program module, as in the present invention. The software may also include modular programming in the form of object-oriented programming. The processing of input data by the processing machine may be in response to user commands, the results of previous processing, or a request made by another processing machine.

As used herein, an element or step recited in the singular and proceeded with the word "a" or "an" should be understood as not excluding plural said elements or steps, unless such exclusion is explicitly recited. Furthermore, references to "one embodiment" or "an embodiment" of the present invention are not intended to be interpreted as excluding the existence of additional embodiments that also incorporate the recited features.

Further, as used herein the term, "image", broadly refers to both viewable images and data representing a viewable image. However, many embodiments generate (or are configured to generate) at least one viewable image.

While the invention has been described in terms of various specific embodiments, those skilled in the art will recognize that the invention can be practiced with modification within the spirit and scope of the claims.

What is claimed is:

1. A method of adjusting a beam spot width, said method comprising:
    scanning a phantom comprising a plurality of rods with an electron beam having a beam spot width to obtain data; and
    adjusting the beam spot width using the obtained data.

2. A method in accordance with claim 1 wherein said scanning comprises scanning a phantom with an electron beam computed tomography system (EBCT) system having a beam spot width to obtain x-ray data, said adjusting comprises adjusting the beam spot width using the obtained x-ray data.

3. A method in accordance with claim 1, wherein said scanning comprises scanning a phantom comprising a plurality of rods, wherein at least one rod is positioned substantially centered in the phantom, and at least some other rods are positioned substantially in a circle.

4. A method in accordance with claim 1, wherein said scanning comprises scanning a phantom comprising a plurality of rods, wherein at least one rod is positioned substantially centered in the phantom, and all other rods are positioned substantially in a circle.

5. A method in accordance with claim 2, wherein said adjusting the beam spot width using the obtained x-ray data comprises:
    generating a normalized sinogram from the obtained data and a scan without the phantom present;
    identifying an object within the phantom on the sinogram;
    generating a profile of the object;
    deconvolving the profile to obtain a beam spot width estimate; and
    adjusting a focal spot parameter to adjust beam spot width.

6. A method in accordance with claim 5, wherein said adjusting a focal spot parameter comprises adjusting a current to a focus coil.

7. A method in accordance with claim 5, wherein said identifying an object comprises identifying a plurality of pin centers on the sinogram.

8. A method in accordance with claim 5, wherein said identifying an object comprises identifying a plurality of pin centers on the sinogram including single pin centers and multiple pin centers, said generating a profile of the object comprises generating a profile of the object using only the single pin centers.

9. A method in accordance with claim 5 further comprising:
    scanning the phantom with the EBCT system having the adjusted beam spot width to obtain second x-ray data;
    generating a second normalized sinogram from the second obtained data and a scan without the phantom present;
    identifying an object within the phantom on the second sinogram;
    generating a second profile of the object;
    deconvolving the second profile to obtain a second beam spot width estimate; and
    adjusting a focal spot parameter to readjust beam spot width.

10. A method in accordance with claim 1 further comprising repeatedly scanning the object and adjusting the beam spot width until a substantially minimum beam spot width is obtained.

11. A method in accordance with claim 2, wherein said adjusting the beam spot width using the obtained x-ray data comprises:
    generating a normalized sinogram from the obtained data and a scan without the phantom present;
    identifying an object within the phantom on the sinogram;
    generating a profile of the object;
    generating a beam spot width estimate; and
    adjusting a focal spot parameter to adjust beam spot width.

12. A method in accordance with claim 11 wherein said generating a beam spot width estimate comprises generating a beam spot width estimate by calculating a full width half maximum value of the generated profile.

13. A method in accordance with claim 11 wherein said generating a beam spot width estimate comprises generating a beam spot width estimate by determining a center of an edge of the object from oversampled and filtered x-ray data.

14. A method in accordance with claim 11 wherein said generating a beam spot width estimate comprises generating a beam spot width estimate by determining a duration of time for the beam spot to be completely occluded.

15. An electron beam computed tomography (EBCT) system comprising:
    an electron beam source configured to emit an electron beam;
    a target positioned to be impinged with the electron beam and radiate x-rays;
    a detector positioned to receive the x-rays; and
    a computer operationally coupled to said detector and said source, said computer configured to:
        receive x-ray data regarding a scanned phantom comprising a plurality of rods; and
        adjust a beam spot width of the emitted electron beam using the received x-ray data.

16. An EBCT system in accordance with claim 15, wherein said computer further configured to repeatedly receive x-ray data regarding the scanned phantom and adjust the beam spot width until a substantially minimum beam spot width is obtained.

17. An EBCT system in accordance with claim 15, wherein said computer further configured to:
    generate a normalized sinogram from the received data and a scan without the phantom present;
    identify an object within the phantom on the sinogram;
    generate a profile of the object;
    deconvolve the profile to obtain a beam spot width estimate; and
    adjust a focal spot parameter to adjust beam spot width.

18. An EBCT system in accordance with claim 17, wherein said computer further configured to:
    identify a plurality of pin centers on the sinogram including single pin centers and multiple pin centers;
    generate a profile of the object using only the single pin centers; and
    adjust a focal spot parameter by adjusting a current to a focus coil.

19. An EBCT system in accordance with claim 18, wherein said computer further configured to repeatedly receive x-ray data regarding the scanned phantom and adjust the current to a focus coil until a substantially minimum beam spot width is obtained.

20. A computer readable medium encoded with a program configured to instruct a computer to:
  repeatedly receive and analyze data regarding a scanned phantom comprising a plurality of rods; and
  repeatedly adjust a beam spot width until a substantially minimum beam spot width is obtained.

21. A computer readable medium in accordance with claim 20, wherein said program further configured to instruct a computer to repeatedly receive and analyze x-ray data regarding the scanned phantom.

22. A computer readable medium in accordance with claim 21, wherein said program further configured to instruct a computer to:
  generate at least one normalized sinogram from the received data and a scan without the phantom present;
  identify an object within the phantom on the sinogram;
  generate a profile of the object;
  generate a beam spot width estimate; and
  adjust a focal spot parameter to adjust beam spot width.

23. A method of providing a malfunction indication, said method comprising:
  repeatedly receiving and analyzing data regarding a scanned phantom comprising a plurality of rods;
  repeatedly adjusting a beam spot width attempting to obtain a desired beam spot width; and
  providing an indication when the desired beam spot width is unobtainable.

24. A method in accordance with claim 23 wherein said repeatedly receiving and analyzing comprises repeatedly receiving and analyzing x-ray data regarding a scanned phantom.

25. A method in accordance with claim 24 wherein said providing comprises providing a visual indication to a local user.

26. A method in accordance with claim 24 wherein said providing comprises providing an indication over a network.

27. A method for increasing a diagnostic ability, said method comprising:
  scanning an object including an edge substantially centered in a field of view using a first electron beam spot width to obtain first x-ray data;
  using the first x-ray data to obtain a second electron beam spot width less than the first electron beam spot width; and
  scanning a patient using the second electron beam width to obtain diagnostic data superior to that obtainable with the first electron beam spot width.

28. A method in accordance with claim 27 wherein the object is within the patient.

* * * * *